US012805940B2

(12) United States Patent
Hsiao et al.

(10) Patent No.: US 12,805,940 B2
(45) Date of Patent: Nov. 24, 2026

(54) CUSTOMIZED MANDIBULAR PLATE MODEL BUILDING METHOD AND SYSTEM

(71) Applicant: NATIONAL CHENG KUNG UNIVERSITY, Tainan City (TW)

(72) Inventors: Jenn-Ren Hsiao, Tainan City (TW); Chou Ching Lin, Tainan City (TW); Shuwei Tsai, Tainan City (TW); Yang-Kao Wang, Tainan City (TW); Meng Yen Chen, Tainan City (TW); Bernard Haochih Liu, Tainan City (TW); Tzu-Yen Chang, Tainan City (TW); Chi-Lun Lin, Tainan City (TW); Chun-Wei Tang, Tainan City (TW); Ya-Man Huang, Tainan City (TW)

(73) Assignee: NATIONAL CHENG KUNG UNIVERSITY, Tainan City (TW)

( * ) Notice: Subject to any disclaimer, the term of this patent is extended or adjusted under 35 U.S.C. 154(b) by 0 days.

(21) Appl. No.: 18/982,857

(22) Filed: Dec. 16, 2024

(65) Prior Publication Data

US 2026/0137451 A1 May 21, 2026

(30) Foreign Application Priority Data

Nov. 15, 2024 (TW) ................................ 113143931

(51) Int. Cl.
*A61B 34/10* (2016.01)
*A61B 17/80* (2006.01)
(Continued)

(52) U.S. Cl.
CPC .......... *A61B 34/10* (2016.02); *A61B 17/8071* (2013.01); *G06T 7/0012* (2013.01);
(Continued)

(58) Field of Classification Search
CPC .......... A61B 2034/102; A61B 17/8071; A61B 2017/568; A61B 2034/108
See application file for complete search history.

(56) References Cited

U.S. PATENT DOCUMENTS 8,377,105 B2 * 2/2013 Buscher ............ A61B 17/8071 606/286
9,411,939 B2 * 8/2016 Furrer ............... A61B 17/8071
(Continued)

*Primary Examiner* — Zade Coley
(74) *Attorney, Agent, or Firm* — Seed Intellectual Property Law Group LLP

(57) ABSTRACT

The present disclosure proposes a customized mandibular plate model building method and system. The mandibular plate model building method includes: obtaining a mandibular tomography image, identifying a defect area in the mandibular tomography image, importing a preliminary designed image corresponding to the defect area and the mandibular tomography image into a 3D modeling software to adjust the preliminary designed image to create an adjusted image that matches the defect area, receiving a user command indicated designated screw holes, combining the designated screw holes, the adjusted design image and the mandibular tomography image into a to-be-validated design image, performing finite element simulation on geometric parameters of the to-be-validated design image to generate a validated design image, and outputting a customized design image according to a mandibular plate model in the validated design image.

12 Claims, 5 Drawing Sheets

(51) Int. Cl.

| | |
|---|---|
| ***G06T 7/00*** | (2017.01) |
| ***G06T 19/20*** | (2011.01) |
| *A61B 6/50* | (2024.01) |
| *A61B 17/56* | (2006.01) |

(52) U.S. Cl.

CPC .............. *G06T 19/20* (2013.01); *A61B 6/505* (2013.01); *A61B 2017/568* (2013.01); *A61B 2034/108* (2016.02); *G06T 2207/10081* (2013.01); *G06T 2207/30008* (2013.01); *G06T 2207/30052* (2013.01); *G06T 2210/41* (2013.01); *G06T 2219/2004* (2013.01); *G06T 2219/2021* (2013.01)

(56) References Cited

U.S. PATENT DOCUMENTS

| | | | | |
|---|---|---|---|---|
| 10,548,668 | B2 * | 2/2020 | Furrer | A61B 34/10 |
| 10,869,705 | B2 * | 12/2020 | Dubois | A61B 17/151 |
| 11,759,244 | B2 * | 9/2023 | Dubois | A61B 17/151<br>606/280 |
| 2007/0118243 | A1 * | 5/2007 | Schroeder | A61F 2/2875<br>700/98 |
| 2010/0106197 | A1 * | 4/2010 | Buscher | A61B 17/151<br>606/286 |
| 2014/0074438 | A1 * | 3/2014 | Furrer | A61B 17/8071<br>703/1 |
| 2014/0149095 | A1 * | 5/2014 | Davison | A61B 17/15<br>703/7 |
| 2016/0220288 | A1 * | 8/2016 | Dubois | A61B 17/151 |
| 2016/0235487 | A1 * | 8/2016 | Davison | A61B 17/15 |
| 2016/0296290 | A1 * | 10/2016 | Furrer | A61B 34/10 |
| 2017/0014169 | A1 * | 1/2017 | Dean | A61B 17/8071 |
| 2018/0276889 | A1 * | 9/2018 | Zagade | B29C 64/386 |
| 2019/0105058 | A1 * | 4/2019 | Mottini | A61B 34/10 |
| 2022/0168028 | A1 * | 6/2022 | Williams | A61B 17/8071 |
| 2024/0325151 | A1 * | 10/2024 | van Putten | A61F 2/30942 |

* cited by examiner

CUSTOMIZED MANDIBULAR PLATE MODEL BUILDING METHOD AND SYSTEM

CROSS-REFERENCE TO RELATED APPLICATIONS

This non-provisional application claims priority under 35 U.S.C. § 119(a) on Patent Application No(s). 113143931 filed in Republic of China (Taiwan) on Nov. 15, 2024, the entire contents of which are hereby incorporated by reference.

BACKGROUND

1. Technical Field

This disclosure relates to a customized mandibular plate model building method and system.

2. Related Art

Mandibular reconstruction surgery is typically performed on patients requiring partial mandible resection due to trauma or tumor surgery. However, currently used reconstruction plate and fixation system thereof and accessories often fail to precisely restore the anatomical structure of the mandible. Postoperative complications may include fatigue failure, screw loosening, and plate exposure over facial skin, further leading to aesthetic disharmony, abnormal occlusion, chewing and swallowing difficulties, and speech impairment. These issues significantly affect postoperative quality of life and health.

Conventional standardized titanium reconstruction plate comes in only a limited number of specifications, making it incapable of fully accommodating the unique defect pattern of each patient's mandible. In addition, physicians have to manually pre-bend the plate to approximate the patient's mandibular contour, either preoperatively or intraoperatively, before securing the plate with screws. This method not only demands significant labor (e.g., manual pre-bending) or prolongs surgery time (e.g., intraoperative bending) but also fails to accurately restore the mechanical characteristics of the mandible. This may result in postoperative complications such as fatigue fractures of the plate, screw loosening, plate exposure, infection, inflammation, and facial asymmetry. Titanium mesh reconstruction, as a semi-rigid fixation method, carries a higher risk of fracture or fatigue failure and shares similar issues of pre-bending and inability to accurately reconstruct the mandible's appearance and mechanical features. Furthermore, the manufacturing process and geometry of titanium mesh, with its increased granularity, make it more prone to infection. Additionally, reconstructing mandibular defects using the patient's own fibular free flap also fails to precisely restore the mandible's appearance and mechanical characteristics and is associated with poor wound healing in the donor site.

SUMMARY

Accordingly, this disclosure provides a customized mandibular plate model building method and system.

According to one or more embodiment of this disclosure, a customized mandibular plate model building method, performed by a processing device includes: obtaining a mandibular tomography image; identifying at least one defect area in the mandibular tomography image; importing a preliminary design image corresponding to the at least one defect area and the mandibular tomography image into a three-dimensional modeling software to adjust the preliminary design image into an adjusted design image that matches the at least one defect area; receiving a user command indicating a plurality of designated screw holes; combining the plurality of designated screw holes, the adjusted design image and the mandibular tomography image into a to-be-optimized design image; performing a finite element simulation on a plurality of geometric parameters of the to-be-optimized design image to generate an optimized design image; and outputting a customized design image according to a mandibular plate model in the optimized design image According to one or more embodiment of this disclosure, a customized mandibular plate model building system includes a memory device and a processing device. The memory device is configured to store a mandibular tomography image. The processing device is connected to the memory device. The processing device is configured to identify at least one defect area in the mandibular tomography image; import a preliminary design image corresponding to the at least one defect area and the mandibular tomography image into a three-dimensional modeling software to adjust the preliminary design image into an adjusted design image that matches the at least one defect area; receive a user command indicating a plurality of designated screw holes; combine the plurality of designated screw holes, the adjusted design image and the mandibular tomography image into a to-be-optimized design image; perform a finite element simulation on a plurality of geometric parameters of the to-be-optimized design image to generate an optimized design image; and output a customized design image according to a mandibular plate model in the optimized design image.

In view of the above description, the customized mandibular plate model building method and system according to one or more embodiments of the present disclosure may allow the mandibular plate to achieve sufficient material mechanical properties (e.g., rigidity, toughness, fatigue strength) to prevent fatigue failure with the customized design image generated through the finite element simulation and referring to the geometric parameters. Furthermore, by performing finite element simulation based on the designated screw holes, the probability of bone screw loosening may be effectively reduced, thereby enhancing surgical precision, which is particularly beneficial for improving the stability of mandibular plate on the mandibles of patients with osteoporosis or low bone density. In addition, the customized mandibular plate model building method and system according to one or more embodiments of the present disclosure may achieve a tailored design to accommodate individual differences, unconstrained by existing plate products, thereby reducing the occurrence of ill-fitting plates to avoid insufficient fixation, while simultaneously ensuring facial symmetry and aesthetics. The customized mandibular plate model building method and system according to one or more embodiments of the present disclosure may first provide a basic prototype design (preliminary design image) for different mandibular defect areas, then adjustments may be made based on the contours of each patient's mandible, thereby shortening the time required for customized design.

BRIEF DESCRIPTION OF THE DRAWINGS

The present disclosure will become more fully understood from the detailed description given hereinbelow and the accompanying drawings which are given by way of illustration only and thus are not limitative of the present disclosure and wherein.

DETAILED DESCRIPTION

In the following detailed description, for purposes of explanation, numerous specific details are set forth in order to provide a thorough understanding of the disclosed embodiments. According to the description, claims and the drawings disclosed in the specification, one skilled in the art may easily understand the concepts and features of the present invention. The following embodiments further illustrate various aspects of the present invention, but are not meant to limit the scope of the present invention.

Figure 1:
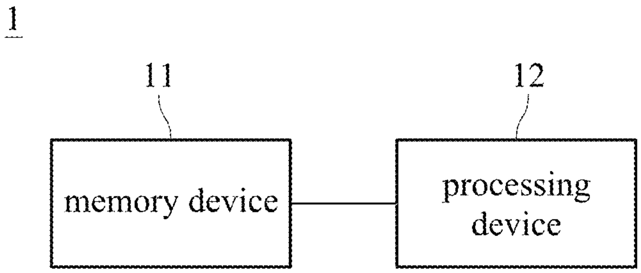
FIG. 1 is a block diagram illustrating a customized mandibular plate model building system according to an embodiment of the present disclosure.

Please refer to FIG. 1, wherein FIG. 1 is a block diagram illustrating a customized mandibular plate model building system according to an embodiment of the present disclosure. As shown in FIG. 1, the customized mandibular plate model building system 1 includes a memory device 11 and a processing device 12. The memory device 11 is in communication with or electrically connected to the processing device 12.

The memory device 11 is configured to store a mandibular tomography image. For example, the mandibular tomography image may be obtained from computed tomography (CT) equipment. The memory device 11 may include one or more memories, the memory may be a non-volatile memory (NVM), such as a read-only memory (ROM), a flash memory and/or a non-volatile random access memory (NVRAM) etc.

The processing device 12 is configured to use the mandibular tomography image to build a corresponding mandibular plate. In addition, the processing device 12 may be connected to one or more of a display screen, a touch screen, a mouse and a keyboard to receive a user command. The processing device 12 may include one or more processors, the processor is, for example, a central processing unit, a graphics processing unit, a microcontroller, a programmable logic controller (PLC) or any other processor with signal processing function.

Figure 2:
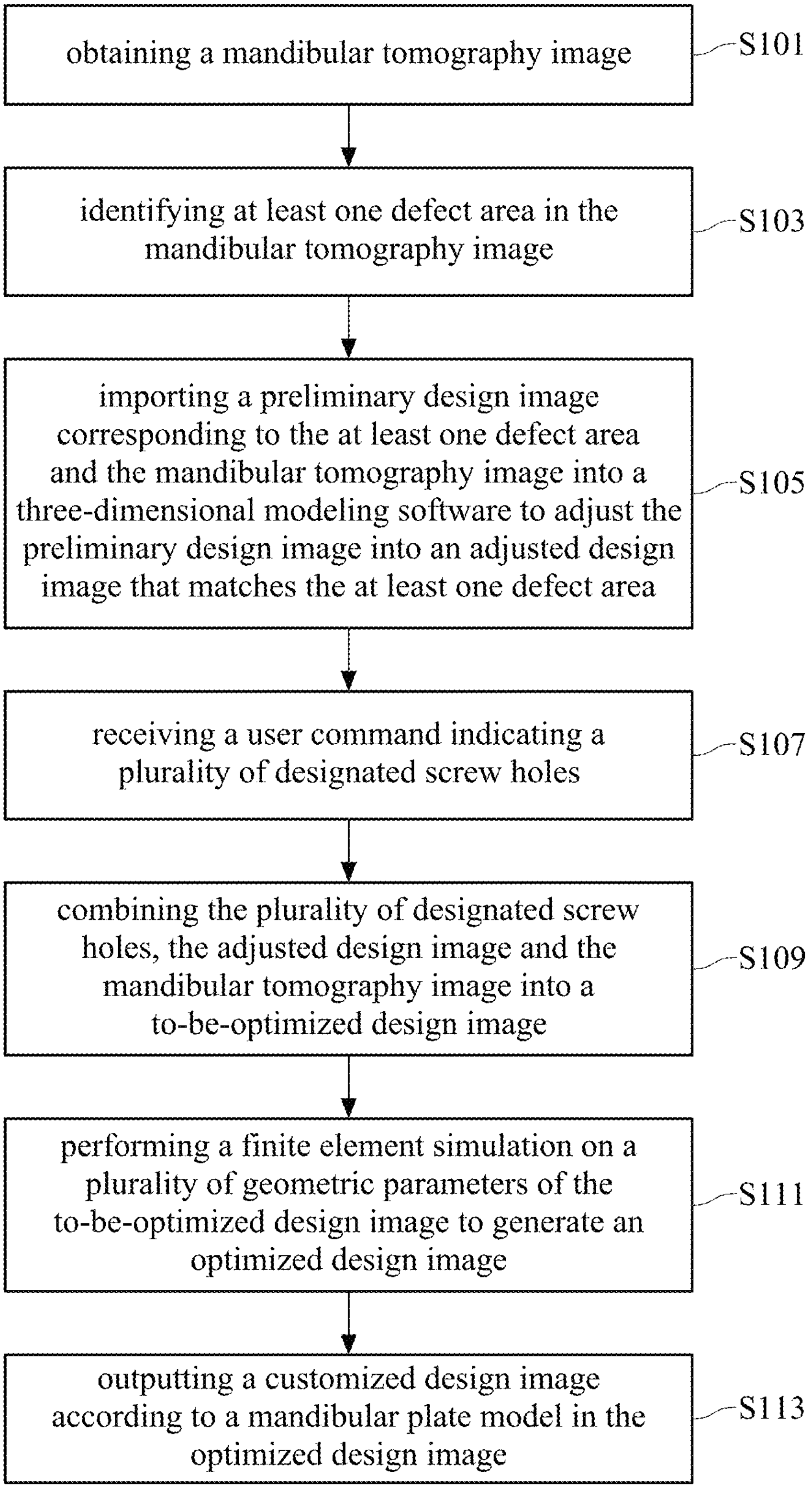
FIG. 2 is a flowchart illustrating a customized mandibular plate model building method according to an embodiment of the present disclosure.
Figure 3A:
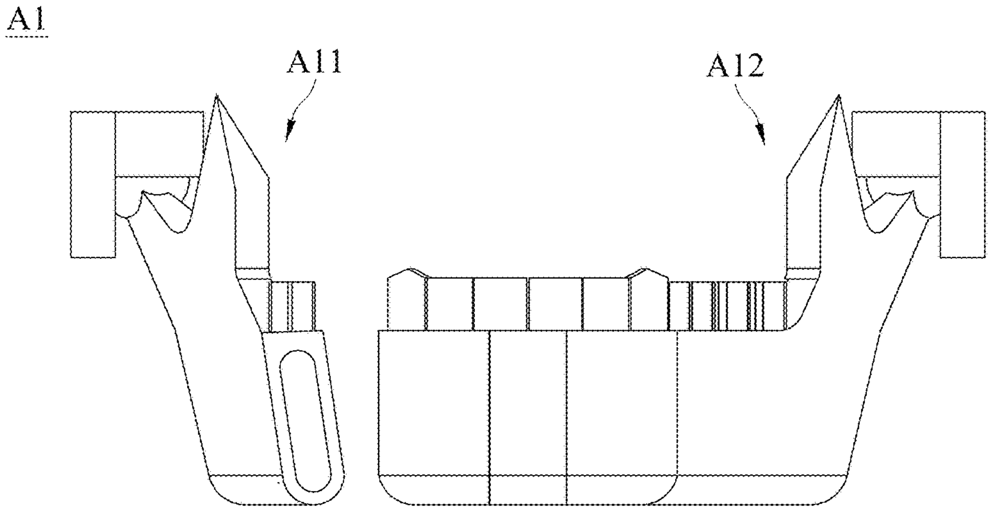
FIG. 3A is a schematic diagram illustrating a mandibular tomography image according to an embodiment of the present disclosure.
Figure 3B:
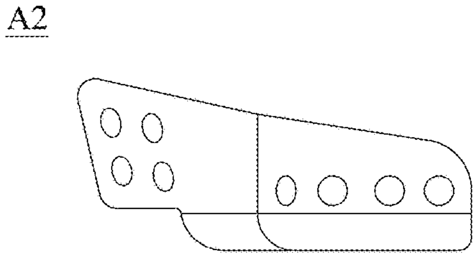
FIG. 3B is a schematic diagram illustrating a preliminary design image according to an embodiment of the present disclosure.
Figure 3C:
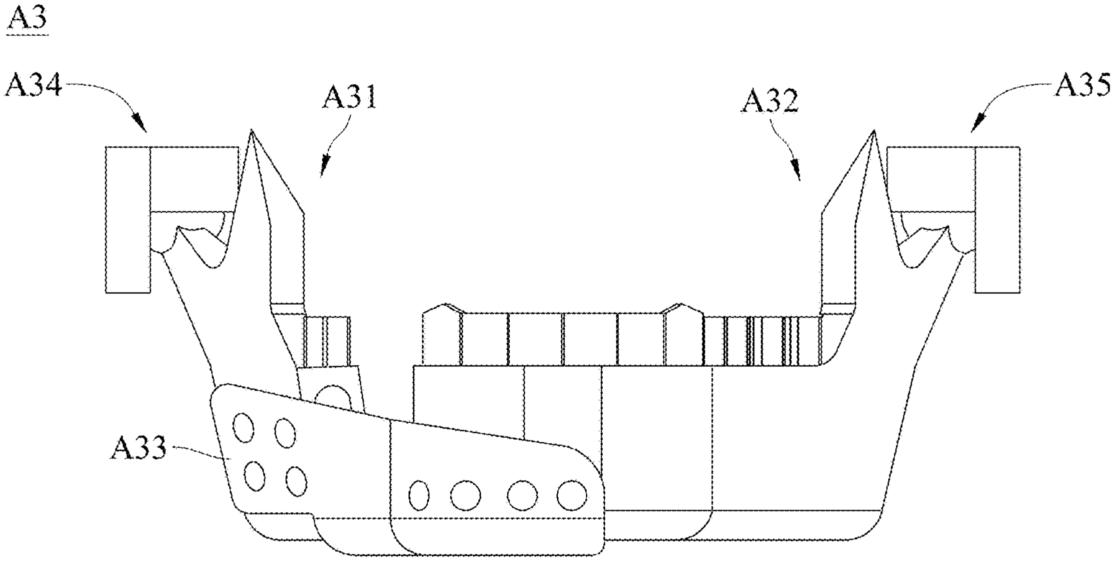
FIG. 3C is a schematic diagram illustrating a to-be-optimized design image according to an embodiment of the present disclosure.

Please refer to FIG. 1, FIG. 2 and FIG. 3A to FIG. 3C, wherein FIG. 2 is a flowchart illustrating a customized mandibular plate model building method according to an embodiment of the present disclosure, FIG. 3A is a schematic diagram illustrating a mandibular tomography image according to an embodiment of the present disclosure, FIG. 3B is a schematic diagram illustrating a preliminary design image according to an embodiment of the present disclosure, and FIG. 3C is a schematic diagram illustrating a to-be-optimized design image according to an embodiment of the present disclosure. As shown in FIG. 2, the customized mandibular plate model building method includes: step S101: obtaining a mandibular tomography image; step S103: identifying at least one defect area in the mandibular tomography image; step S105: importing a preliminary design image corresponding to the at least one defect area and the mandibular tomography image into a three-dimensional modeling software to adjust the preliminary design image into an adjusted design image that matches the at least one defect area; step S107: receiving a user command indicating a plurality of designated screw holes; step S109: combining the plurality of designated screw holes, the adjusted design image and the mandibular tomography image into a to-be-optimized design image; step S111: performing a finite element simulation on a plurality of geometric parameters of the to-be-optimized design image to generate an optimized design image; and step S113: outputting a customized design image according to a mandibular plate model in the optimized design image. The present disclosure does not limit the sequence of performing step S107 and step S105, step S107 may be performed before step S105 or performed at the same time as step S105. Even though FIG. 2 illustrates step S107 as performed after step S105, FIG. 2 does not intend to limit that step S107 is performed only after generating the adjusted design image. For example, step S107 may be performed as soon as the preliminary design image is obtained.

In step S101, the processing device 12 obtains the mandibular tomography image from the memory device 11. For example, the processing device 12 may directly obtain a head tomography image from the computed tomography (CT) equipment, or the memory device 11 may store the head tomography image, and the head tomography image stored by the memory device 11 may be obtained from the CT equipment. An embodiment of step S101 may include obtaining the head tomography image, and removing a plurality of non-mandibular blocks from the head tomography image to generate the mandibular tomography image. The non-mandibular blocks may include soft tissue images and hard tissue images not belonging to mandible. Further, the processing device 12 may remove the non-mandibular blocks by using 3D slicer software.

In step S103, the processing device 12 determines one or more defect areas in the mandibular tomography image. Please refer to FIG. 3A, the mandibular tomography image A1 includes a first area A11 and a second area A12, and a spacing (i.e. a part of the bone that is missing from the mandible) between the first area A11 and the second area A12 may be regarded as the defect area. It should be noted that FIG. 3A schematically shows one defect area, according to the patient's condition, the mandibular tomography image may also include multiple defect areas.

In addition, the processing device 12 may divide the mandibular tomography image A1 in to a body (B) part, a symphysis(S) part, a ramus (R) part, a hemisymphysis ($S_H$) part and a condyle (C) part. According to the location of the defect area in the mandibular tomography image A1, the processing device 12 may further determine the type of the defect area being BSB, RB, RBS, $RBS_H$, CRB, BS, RBSB, CRBS, B, $BS_H$, RBSBR, $CRBS_H$, CR etc.

In step S105, the processing device 12 imports the preliminary design image corresponding to the defect area and the mandibular tomography image into the three-dimensional modeling software, to adjust the preliminary design image into matching the mandibular tomography image. Such adjustment may be performed automatically by the processing device 12 or by manually by the user. The preliminary design image may be a three-dimensional design image of the mandibular plate, and the preliminary design image may be designed according to the type of the defect area. For example, the memory device 11 may further store a plurality of candidate design images corresponding to different types of defect areas, and the processing device 12 may select one of the candidate design images according to the defect area corresponding to the mandibular tomography image as the preliminary design image. The three-dimensional modeling software may be Meshmixer. As shown in FIG. 3A, the processing device 12 adjusts two ends of the plate of the preliminary design image respectively into fitting a part of the first area A11 that is close to the defect area and a part of the second area A12 that is close to the defect area according to the location and type of the defect area in the mandibular tomography image A1. The processing device 12 uses the adjusted preliminary design image as the adjusted design image.

In step S107, the processing device 12 receives the user command designating the designated screw holes, wherein the designated screw holes may not be at locations corresponding to mental foramen in the mandibular tomography image A1.

In step S109, the processing device 12 combines the designated screw holes, the adjusted design image and the mandibular tomography image into the to-be-optimized design image. For example, the processing device 12 may first combine the designated screw holes and the adjusted design image into the adjusted design image A2 as shown in FIG. 3B, and then combine the mandibular tomography image A1 and the adjusted design image A2 into the to-be-optimized design image A3 as shown in FIG. 3C. The sequence of combining the images described above is merely an example, the present disclosure is not limited thereto. Accordingly, the to-be-optimized design image A3 includes the first area A31, the second area A32 and the adjusted design image A33 including the designated screw holes, wherein the first area A31 and the second area A32 may be the same as the first area A11 and the second area A12 of FIG. 3A, respectively. In an embodiment, the to-be-optimized design image A3 may further include surrounding tissues A34 and A35 of the mandible. For example, the surrounding tissue A34 of the mandible may include the right cranial bone and the right ligament, and the surrounding tissue A35 of the mandible may include the left cranial bone and the left ligament. Accordingly, the finite element simulation subsequently performed on the to-be-optimized design image A3 may be more accurate.

In step S111, the processing device 12 performs a design optimization process based on the finite element simulation on the geometric parameters and a shape of the to-be-optimized design image A3 to adjust the mechanical properties and geometric structure etc. of the to-be-optimized design image A3. Further, the processing device 12 may import the to-be-optimized design image A3 into a mesh generating software (such as HyperMesh) to establish a three dimensional mesh of the to-be-optimized design image A3, and import the three dimensional mesh into a finite element analysis software (such as Abaqus) to establish a finite element model. Further, the processing device 12 may set material properties, loading condition, contact interaction, and boundary conditions, where the mandible is assigned material properties based on bone density derived from the corresponding tomographic image. The loading condition should account for various forms of occlusion. The geometric parameters may include at least one of a shape corresponding to the to-be-optimized design image, thickness corresponding to the to-be-optimized design image and locations corresponding to the designated screw holes, wherein the shape corresponding to the to-be-optimized design image may include the contour of the mandibular plate model (i.e. the adjusted design image) in the to-be-optimized design image. The thickness corresponding to the to-be-optimized design image may be thickness(s) of one or more parts of the mandibular plate model in the to-be-optimized design image. The geometric parameters may further include one or more of whether the bone plate covers the lower side of the mandible and the density of specified bone screw holes. In addition, during the finite element simulation, the processing device 12 may utilize the design optimization method, such as particle swarm optimization (PSO) or bidirectional evolutionary structural optimization (BESO), to generate the optimized design image.

In step S113, the processing device 12 uses the mandibular plate model in the optimized design image to output the customized design image. In an embodiment, step S113 may include the processing device 12 using the mandibular plate model in the optimized design image as the customized design image.

Since mandibles of different patients may require designs with varying thicknesses and positions of bone screw holes, step S111 may help avoid excessive rigidity of the mandibular plate, which could lead to suboptimal recovery of the mandible. Step S111 may also prevent the bone screw holes from being located too close to each other, which could result in stress concentration issue.

In addition, the processing device 12 may use the finite element simulation and the bidirectional evolutionary structural optimization algorithm to verify the rigidity of the optimized design image after the adjustment, and the adjustment and verifying the optimized design image may be performed repeatedly. Specifically, in another embodiment of step S113, the processing device 12 may determine whether a value of a target parameter corresponding to the mandibular plate model in the optimized design image is equal to or greater than a default value, and may use the mandibular plate model as the customized design image when determining the value of the target parameter is equal to or greater than the default value. The target parameter may include a mechanical parameter, which includes one or more of the following: the stress value borne by the mandibular plate model, the strain value borne by the mandibular plate model, the total weight of the mandibular plate model, and the material consumption of the mandibular plate model. The corresponding default value may include a default mechanical value limit, which includes one or more of the following: the upper limit of stress that the mandibular plate model can bear, the upper limit of strain that the mandibular plate model can bear, the upper limit of the weight of the mandibular plate model, and the upper limit of material consumption of the mandibular plate model.

On the contrary, when the value of the target parameter corresponding to the mandibular plate model in the optimized design image is smaller than the default value, the processing device 12 may adjust the values of the geometric parameters of the optimized design image, and perform step S111 on the adjusted optimized design image again. In other words, the processing device 12 may perform the finite element simulation on the geometric parameters of the optimized design image to generate another optimized design image, and perform step S111 on said another optimized design image. The steps of determining whether the value of the target parameter corresponding to the mandibular plate model is equal to or greater than the default value and adjusting the mandibular plate model when the value of the target parameter is smaller than the default value may be implemented with bidirectional evolutionary structural optimization.

In yet another embodiment of step S113, the processing device 12 may be triggered by a user command to use the mandibular plate model in the optimized design image as the customized design image, wherein the user command may indicate the convergence of differences between the pre-adjustment and post-adjustment of the optimized design image based on the bidirectional evolutionary structural optimization method.

Accordingly, the customized mandibular plate model building method and system according to one or more embodiments of the present disclosure may allow the mandibular plate to achieve sufficient material mechanical properties (e.g., rigidity, toughness, fatigue strength) to prevent fatigue failure with the customized design image generated through the finite element simulation and referring to the geometric parameters. Furthermore, by performing finite element simulation based on the designated screw holes, the probability of bone screw loosening may be effectively reduced, thereby enhancing surgical precision, which is particularly beneficial for improving the stability of mandibular plate on the mandibles of patients with osteoporosis or low bone density. In addition, the customized mandibular plate model building method and system according to one or more embodiments of the present disclosure may achieve a tailored design to accommodate individual differences, unconstrained by existing plate products, thereby reducing the occurrence of ill-fitting plates to avoid insufficient fixation, while simultaneously ensuring facial symmetry and aesthetics. The customized mandibular plate model building method and system according to one or more embodiments of the present disclosure may first provide a basic prototype design (preliminary design image) for different mandibular defect areas, then adjustments may be made based on the contours of each patient's mandible, thereby shortening the time required for customized design.

Figure 4:
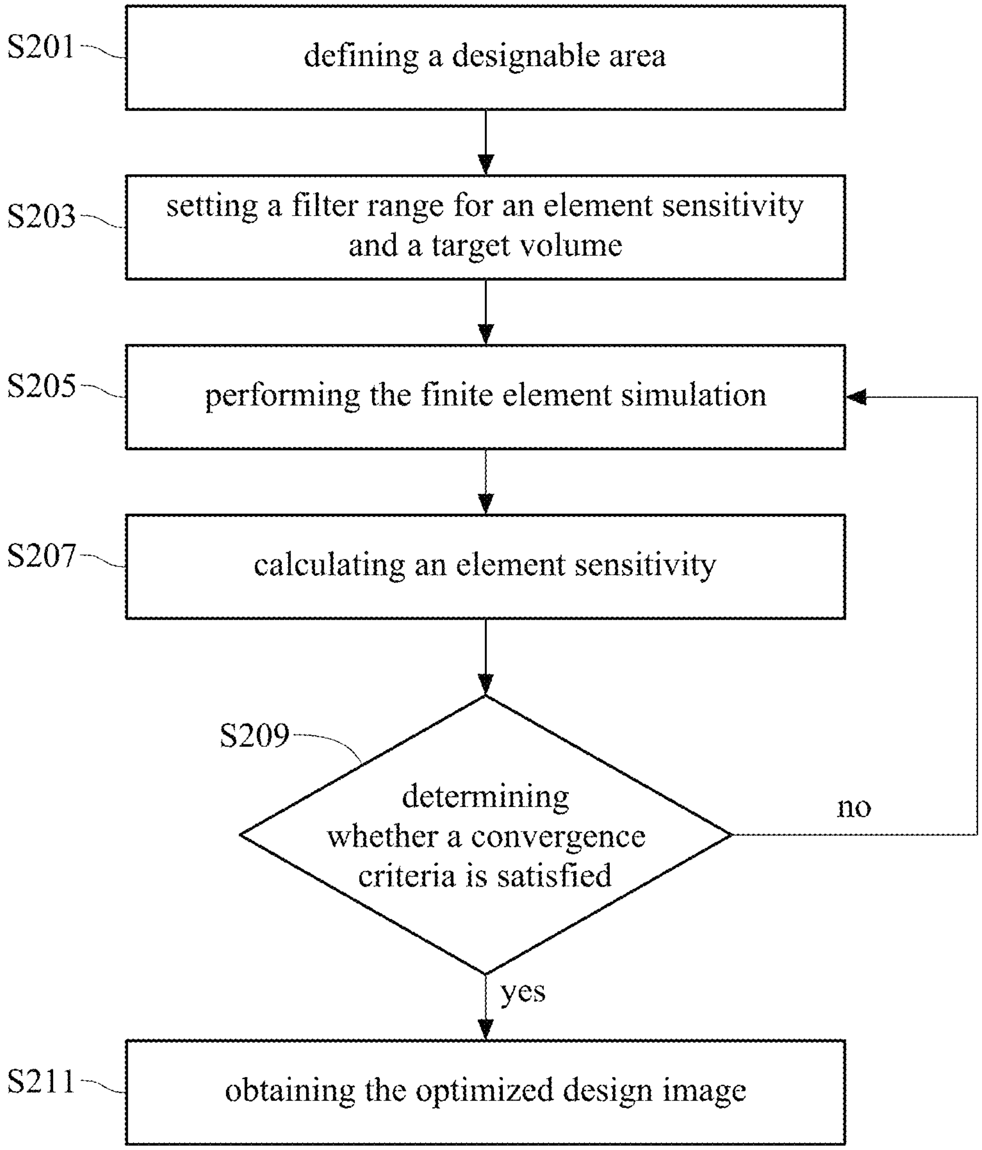
FIG. 4 is a flowchart illustrating performing design optimization on the to-be-optimized design image based on finite element analysis according to an embodiment of the present disclosure.

Please refer to FIG. 1 and FIG. 4, wherein FIG. 4 is a flowchart illustrating performing design optimization on the to-be-optimized design image based on finite element analysis according to an embodiment of the present disclosure. FIG. 4 may be regarded as a detailed flowchart of an embodiment of step S111 of FIG. 2. As shown in FIG. 4, performing the finite element simulation on the to-be-optimized design image may include: step S201: defining a designable area; step S203: setting a filter range for an element sensitivity in the designable area and a target volume; step S205: performing finite element simulation; step S207: calculating an element sensitivity; step S209: determining whether the convergence condition is satisfied; when the determination result of step S209 is "yes", performing step S211: obtaining the optimized design image; and when the determination result of step S209 is "no", performing step S205 again. Steps S205, S207 and S209 may be regarded as a first simulation procedure.

In step S201, the processing device 12 may define a designable area and a non-designable area in the to-be-optimized design image. The designable area is one or more portions in the to-be-optimized design image where values of various parameters and materials used are allowed to be adjusted. The non-designable area is one or more portions in the to-be-optimized design image where values of various parameters and materials used are fixed.

In step S203, the processing device 12 may set the filter range for the element sensitivity in the designable area and the target volume to obtain a to-be-simulated design image. The element sensitivity may represent the rigidity of the designable area or the to-be-optimized design image. The filter range for the element sensitivity may represent the optimization evolution speed. The target volume may be a desired volume of the mandibular plate model of the final design image.

In step S205, the processing device 12 may perform the finite element simulation on the to-be-simulated design image to obtain a stress-strain distribution. In other words, through step S205, the processing device 12 may obtain the stress-strain distribution of the current bone plate structure in the to-be-simulated design image under loading condition.

In step S207, the processing device 12 may delete at least one element from the to-be-simulated design image according to the stress-strain distribution to obtain a first updated design image. Further, the processing device 12 may calculate the sensitivity of each element in the mesh of the to-be-simulated design image through the bidirectional evolutionary structural optimization, and delete one or more elements with sensitivities lower than a default sensitivity. The sensitivity may indicate rigidity, stress distribution etc. The processing device 12 may use the to-be-simulated design image with element(s) deleted as the first updated design image.

In step S209, the processing device 12 may determine whether an updated volume of the first updated design image matches the target volume to check whether the volume of the material of the plate after the update satisfies the convergence condition. When the processing device 12 determines the updated volume of the first updated design image matches the target volume, the processing device 12 may determine the convergence condition is satisfied, and the processing device 12 proceeds to perform step S211.

In step S211, the processing device 12 may determine the shape of the first updated design image has been optimized, and the processing device 12 may obtain the optimized design image according to the first updated design image. For example, the processing device 12 may directly use the first updated design image as the optimized design image.

It should be noted that the designable area and the non-designable area, the filter range of the element sensitivity, the target volume and the default sensitivity may be set by the processing device 12 according to a user command.

Figure 5:
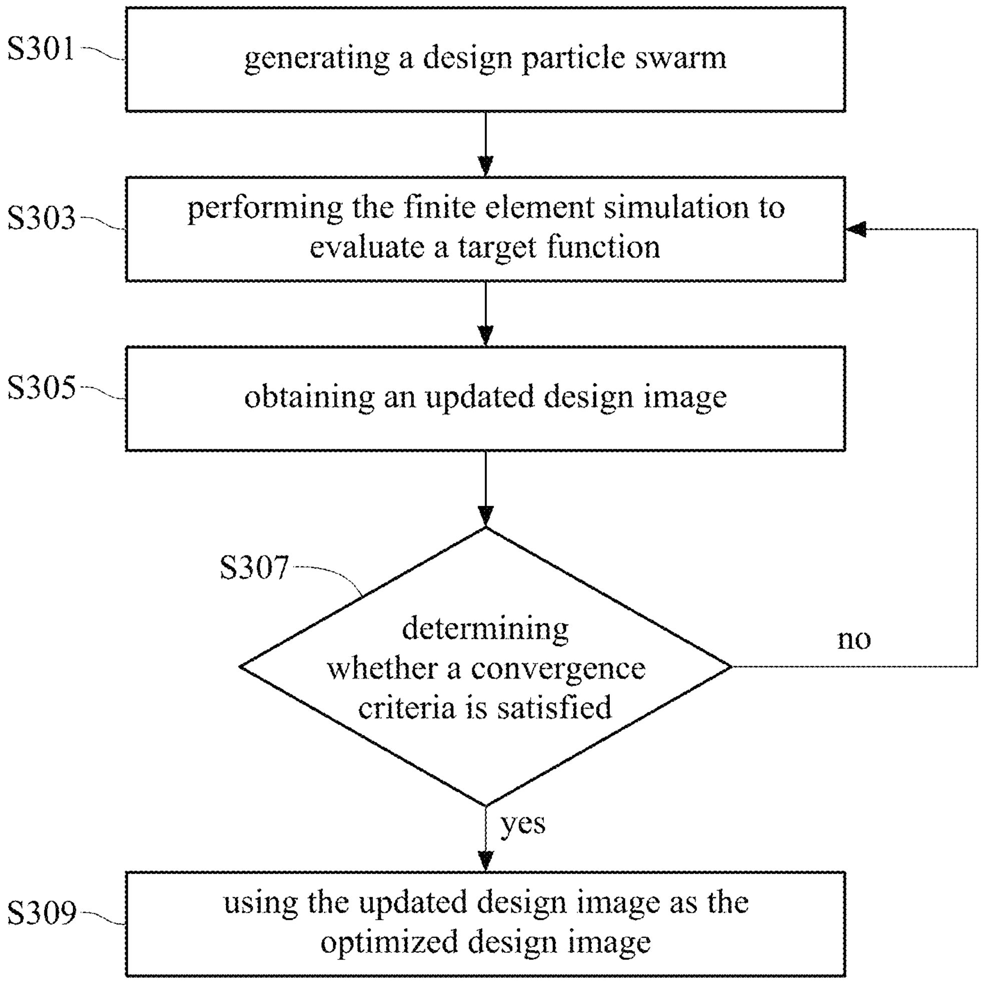
FIG. 5 is a flowchart illustrating performing design optimization on an updated design image based on finite element analysis according to an embodiment of the present disclosure.

Please refer to FIG. 1 and FIG. 5, wherein FIG. 5 is a flowchart illustrating performing design optimization on an updated design image based on finite element analysis according to an embodiment of the present disclosure. FIG. 5 may be regarded as a detailed flowchart of step S211 of FIG. 4. As shown in FIG. 5, performing the finite element simulation on the updated design image may include: step S301: generating a design particle swarm; step S303: performing the finite element simulation to evaluate a target function; step S305: obtaining the updated design image; step S307: determining whether the convergence condition is satisfied; when the determination result of step S307 is "yes", performing step S309: using the updated design image as the optimized design image; and when the determination result of step S307 is "no", performing step S303 again. Steps S303, S305 and S307 may be regarded as a second simulation procedure.

In step S301, the processing device 12 may perform particle swarm optimization algorithm on the first updated design image to obtain the design particle swarm. The design particle swarm includes a plurality of design points, and the design points include variables of different combinations. The variable is a variable of a design parameter or a mandible attribute. In addition, before performing step S301, the processing device 12 may define the design parameter of the first updated design image, such as the number of holes, the locations of the holes and plate thickness, etc.

In step S303, the processing device 12 may perform the finite element simulation on the design particle swarm to obtain a current mechanical function (target function). In other words, the processing device 12 may determine the mechanical indicator of the mandible and/or bone plate as the current mechanical function, wherein the current mechanical function indicates the maximum stress/strain or the regional average stress/strain applied on the mandible and/or bone plate under the set loading condition.

In step S305, the processing device 12 may update the first updated design image according to the current mechanical function to obtain a second updated design image. Specifically, the current design point group is applied to determine the update strategy for this iteration based on the group's optimal target function value, the individual optimal target function value, and the previous update direction.

In step S307, the processing device 12 may determine whether an iteration indicator of the second updated design image matches a convergence indicator, to determine whether the second updated design image satisfies the convergence condition. The iteration indicator may include one or more of the mechanical indicator, the degree of improvement compared to the previous second updated design image, and/or the number of iterations. The mechanical indicator may represent the maximum stress/strain or the regional average stress/strain of the mandible and/or bone plate under the specified loading condition.

When the processing device 12 determines the mechanical indicator of the second updated design image reaches (equal to or greater than) the default indicator, the degree of improvement reaches (equal to or greater than) a default degree and/or the number of iterations reaches (equal to or greater than) a default number (set by the processing device), the processing device 12 then performs step S309. In step S309, the processing device 12 may determine that the design parameters of the second updated design image has been optimized, and the processing device 12 may directly use the second updated design image as the optimized design image.

On the contrary, when the processing device 12 determines the mechanical indicator (iteration indicator) of the second updated design image does not match the default indicator (convergence indicator), the degree of improvement does not reach the default degree and/or the number of iterations does not reach the default number, the processing device 12 performs the particle swarm optimization on the second updated design image to obtain another design particle swarm, and performs step S303 on said another design particle swarm.

It should be noted that the design parameter and the convergence indicator of the first updated design image may be set by the processing device 12 according to a user command.

In view of the above description, the customized mandibular plate model building method and system according to one or more embodiments of the present disclosure may allow the mandibular plate to achieve sufficient material mechanical properties (e.g., rigidity, toughness, fatigue strength) to prevent fatigue failure with the customized design image generated through the finite element simulation and referring to the geometric parameters. Furthermore, by performing finite element simulation based on the designated screw holes, the probability of bone screw loosening may be effectively reduced, thereby enhancing surgical precision, which is particularly beneficial for improving the stability of mandibular plate on the mandibles of patients with osteoporosis or low bone density. In addition, the customized mandibular plate model building method and system according to one or more embodiments of the present disclosure may achieve a tailored design to accommodate individual differences, unconstrained by existing plate products, thereby reducing the occurrence of ill-fitting plates to avoid insufficient fixation, while simultaneously ensuring facial symmetry and aesthetics. The customized mandibular plate model building method and system according to one or more embodiments of the present disclosure may first provide a basic prototype design (preliminary design image) for different mandibular defect areas, then adjustments may be made based on the contours of each patient's mandible, thereby shortening the time required for customized design. Further, through the mechanism of determining whether the value of the target parameter (for example, the amount of material used, the weight of the mandibular plate) corresponds to the mandibular plate model is equal to or greater than the default value, the amount of material used and cost may be reduced.

What is claimed is:

1. A customized mandibular plate model building method, performed by a processing device, the method comprising:

obtaining a mandibular tomography image;

identifying at least one defect area in the mandibular tomography image;

importing a preliminary design image corresponding to the at least one defect area and the mandibular tomography image into a three-dimensional modeling software to adjust the preliminary design image into an adjusted design image that matches the at least one defect area;

receiving a user command indicating a plurality of designated screw holes;

combining the plurality of designated screw holes, the adjusted design image and the mandibular tomography image into a to-be-optimized design image;

performing a finite element simulation on a plurality of geometric parameters of the to-be-optimized design image to generate an optimized design image; and outputting a customized design image according to a mandibular plate model in the optimized design image, wherein performing the finite element simulation on the plurality of geometric parameters of the to-be-optimized design image to generate the optimized design image comprises:

defining a designable area in the to-be-optimized design image;

setting a filter range for an element sensitivity in the designable area and a target volume to obtain a to-be-simulated design image;

performing a first simulation procedure, comprising:

performing the finite element simulation on the to-be-simulated design image to obtain a stress-strain distribution;

deleting at least one element from the to-be-simulated design image according to the stress-strain distribution to obtain a first updated design image; and determining whether an updated volume of the first updated design image matches the target volume;

using the first updated design image as another to-be-simulated design image and performing the first simulation procedure again when the updated volume does not match the target volume; and obtaining the optimized design image according to the first updated design image when the updated volume matches the target volume.

2. The customized mandibular plate model building method according to claim 1, wherein the plurality of geometric parameters comprise at least one of: a shape corresponding to the to-be-optimized design image, a thickness corresponding to the to-be-optimized design image, locations of the plurality of designated screw holes and a bone density corresponding to the mandibular tomography image.

3. The customized mandibular plate model building method according to claim 1, wherein outputting the customized design image according to the mandibular plate model in the optimized design image comprises:

determining whether a value of a target parameter corresponding to the mandibular plate model in the optimized design image equal to or greater than a default value; and using the mandibular plate model as the customized design image when the value of the target parameter corresponding to the mandibular plate model in the optimized design image equal to or greater than the default value.

4. The customized mandibular plate model building method according to claim 1, wherein obtaining the mandibular tomography image comprises:

obtaining a head tomography image; and removing a plurality of non-mandibular blocks from the head tomography image to generate the mandibular tomography image.

5. The customized mandibular plate model building method according to claim 1, wherein obtaining the optimized design image according to the first updated design image comprises:

performing a particle swarm optimization algorithm on the first updated design image to obtain a design particle swarm;

performing a second simulation procedure, comprising:

performing the finite element simulation on the design particle swarm to obtain a current mechanical function;

updating the first updated design image according to the current mechanical function to obtain a second updated design image; and determining whether an iteration indicator of the second updated design image matches a convergence indicator;

performing the particle swarm optimization algorithm on the second updated design image to obtain another design particle swarm and performing the second simulation procedure again when the iteration indicator does not match the convergence indicator; and using the second updated design image as the optimized design image when the iteration indicator matches the convergence indicator.

6. The customized mandibular plate model building method according to claim 1, wherein performing the finite element simulation on the plurality of geometric parameters of the to-be-optimized design image to generate the optimized design image comprises: using a bidirectional evolutionary structural optimization algorithm.

7. A customized mandibular plate model building system, comprising:

a memory device configured to store a mandibular tomography image; and a processing device connected to the memory device, the processing device configured to identify at least one defect area in the mandibular tomography image; import a preliminary design image corresponding to the at least one defect area and the mandibular tomography image into a three-dimensional modeling software to adjust the preliminary design image into an adjusted design image that matches the at least one defect area; receive a user command indicating a plurality of designated screw holes; combine the plurality of designated screw holes, the adjusted design image and the mandibular tomography image into a to-be-optimized design image; perform a finite element simulation on a plurality of geometric parameters of the to-be-optimized design image to generate an optimized design image; and output a customized design image according to a mandibular plate model in the optimized design image, wherein the processing device is configured to perform:

defining a designable area in the to-be-optimized design image;

setting a filter range for an element sensitivity in the designable area and a target volume to obtain a to-be-simulated design image;

performing a first simulation procedure, comprising:

performing the finite element simulation on the to-be-simulated design image to obtain a stress-strain distribution;

deleting at least one element from the to-be-simulated design image according to the stress-strain distribution to obtain a first updated design image; and determining whether an updated volume of the first updated design image matches the target volume;

using the first updated design image as another to-be-simulated design image and performing the first simulation procedure again when the updated volume does not match the target volume; and obtaining the optimized design image according to the first updated design image when the updated volume matches the target volume.

8. The customized mandibular plate model building system according to claim 7, wherein the plurality of geometric parameters comprise at least one of: a shape corresponding to the to-be-optimized design image, a thickness corresponding to the to-be-optimized design image, locations of the plurality of designated screw holes and a bone density corresponding to the mandibular tomography image.

9. The customized mandibular plate model building system according to claim 7, wherein the processing device is configured to determine whether a value of a target parameter corresponding to the mandibular plate model in the optimized design image equal to or greater than a default value, and use the mandibular plate model as the customized design image when the value of the target parameter corresponding to the mandibular plate model in the optimized design image equal to or greater than the default value.

10. The customized mandibular plate model building system according to claim 7, wherein the processing device is configured to obtain a head tomography image, and remove a plurality of non-mandibular blocks from the head tomography image to generate the mandibular tomography image.

11. The customized mandibular plate model building system according to claim 7, wherein the processing device is configured to perform:

performing a particle swarm optimization algorithm on the first updated design image to obtain a design particle swarm;

performing a second simulation procedure, comprising:

performing the finite element simulation on the design particle swarm to obtain a current mechanical function;

updating the first updated design image according to the current mechanical function to obtain a second updated design image; and determining whether an iteration indicator of the second updated design image matches a convergence indicator;

performing the particle swarm optimization algorithm on the second updated design image to obtain another design particle swarm and performing the second simulation procedure again when the iteration indicator does not match the convergence indicator; and using the second updated design image as the optimized design image when the iteration indicator matches the convergence indicator.

12. The customized mandibular plate model building system according to claim 7, wherein the processing device is configured to use a bidirectional evolutionary structural optimization algorithm.

* * * * *